United States Patent
Zhang et al.

(10) Patent No.: US 12,150,926 B2
(45) Date of Patent: Nov. 26, 2024

(54) USE OF CHLOROGENIC ACID COMPOSITION THEREOF IN PREPARATION OF MEDICAMENT FOR TREATING SARCOMA

(71) Applicant: SICHUAN JIUZHANG BIOLOGICAL SCIENCE AND TECHNOLOGY CO., LTD., Sichuan (CN)

(72) Inventors: Jie Zhang, Sichuan (CN); Xiaoguang Chen, Sichuan (CN); Wang Huang, Sichuan (CN)

(73) Assignee: SICHUAN JIUZHANG BIOLOGICAL SCIENCE AND TECHNOLOGY CO., LTD, Sichuan (CN)

( * ) Notice: Subject to any disclaimer, the term of this patent is extended or adjusted under 35 U.S.C. 154(b) by 1036 days.

(21) Appl. No.: 17/050,593

(22) PCT Filed: Apr. 24, 2019

(86) PCT No.: PCT/CN2019/083989
§ 371 (c)(1),
(2) Date: Oct. 26, 2020

(87) PCT Pub. No.: WO2019/206159
PCT Pub. Date: Oct. 31, 2019

(65) Prior Publication Data
US 2021/0338622 A1 Nov. 4, 2021

(30) Foreign Application Priority Data
Apr. 24, 2018 (CN) .......................... 201810374587.0

(51) Int. Cl.
*A61K 31/216* (2006.01)
*A61P 35/00* (2006.01)

(52) U.S. Cl.
CPC ............ *A61K 31/216* (2013.01); *A61P 35/00* (2018.01)

(58) Field of Classification Search
CPC .............................. A61K 31/216; A61P 35/00
See application file for complete search history.

(56) References Cited

U.S. PATENT DOCUMENTS

2003/0229140 A1* 12/2003 Bandyopadhyay .. A61K 31/366
514/533
2009/0076131 A1 3/2009 Ricciardiello et al.

FOREIGN PATENT DOCUMENTS

| CN | 1646112 A | 7/2005 |
|---|---|---|
| CN | 108159038 A | 6/2018 |
| CN | 108653263 A | 10/2018 |

OTHER PUBLICATIONS

Cvetanovic et al. "Antioxidant and biological activity of chamomile extracts obtained by different techniques: perspective of using superheated water for isolation of biologically active compounds" Industrial Crops and Products, vol. 65, pp. 582-591. (Year: 2015).*
Aleksandra et al.; "Antioxidant and Biological Activeity of Chamomile Extracts Obtained by Different Techniques: Perspective of Using Superheated Water for Isolation of Biologically Active Compounds"; Industrial Crops and Products, vol. 65, Dec. 31, 2015.

* cited by examiner

*Primary Examiner* — Kamal A Saeed
(74) *Attorney, Agent, or Firm* — NKL Law; Allen Xue

(57) ABSTRACT

Chlorogenic acid or compositions containing chlorogenic acid are used in preparation of a medicament for treating sarcoma. The chlorogenic acid composition includes chlorogenic acid and coumaroyl quinic acid, can effectively treat sarcoma, and has a better therapeutic effect than the chemotherapeutic medicament doxorubicin. The experimental results show that the combination of chlorogenic acid and coumaroylquinic acid can have a synergistic effect.

8 Claims, 4 Drawing Sheets

USE OF CHLOROGENIC ACID COMPOSITION THEREOF IN PREPARATION OF MEDICAMENT FOR TREATING SARCOMA

TECHNICAL FIELD

The present invention particularly relates to the use of chlorogenic acid in the preparation of drugs for treatment of sarcoma. The present invention also relates to the use of the composition containing chlorogenic acid in the preparation of drugs for treatment of sarcoma.

BACKGROUND ART

Sarcomas are malignant tumors originated from mesenchymal tissues (including connective tissues and muscles), which mostly occur in skin, subcutaneous, periosteum and both ends of long bone. Osteosarcoma is more common in young people, and often occurs at both ends of long bones of limbs, especially at the lower end of femur and the upper end of tibia and humerus. Osteosarcoma develops rapidly and has a short course, meanwhile, it originally grows in the cortex and gradually develops into the bone marrow cavity. Sometimes it breaks through the periosteum and invades the surrounding soft tissues, that is easy to cause pathological fracture. Leiomyoma, lymphosarcoma, synovial sarcoma and so on are common, and all of them can cause hematogenous metastasis in the early stage. Sarcoma is a malignant tumor.

At present, the main ways for treatment of sarcoma are surgery, chemotherapy and local radiotherapy. In surgical operations, amputation or radical resection is the most commonly used method, but the therapeutic effect is still unsatisfactory, and about 50% of patients still die, while the therapeutic effect of partial resection is also unsatisfactory. Nowadays, domestic and foreign doctors all tend to retain most of the limbs, followed by chemotherapy. Chemotherapy is feasible before and after surgery, but the effective rate is not high, and the side effects are significant. Local radiotherapy can also be selectively used for some patients with sarcoma, but the effective rate is low, and once lung metastasis occurs, the effect becomes even worse.

Therefore, a drug that can effectively treat sarcoma is urgently needed, and no report on the use of chlorogenic acid in the treatment of sarcoma has been found.

Content of the Invention

The technical solution of the present invention provides the new use of chlorogenic acid.

The use of chlorogenic acid in the preparation of drugs for treatment of sarcoma.

Wherein, said drug is a preparation obtained by using chlorogenic acid as the active ingredient, with the addition of pharmaceutically acceptable excipients or auxiliary ingredients.

Wherein, said pharmaceutical preparation contains 1-3000 mg chlorogenic acid/unit.

Wherein, the dosage of chlorogenic acid in said pharmaceutical preparation is 1-100 mg/kg.

Wherein, said medicament is an oral preparation or an injection.

Wherein, said sarcoma includes osteosarcoma, fibrosarcoma, liposarcoma, and rhabdomyosarcoma. The present invention further provides a pharmaceutical composition, that contains chlorogenic acid and coumaroylquinic acid.

Further, the mass ratio of chlorogenic acid to coumaroylquinic acid is 100:0.01-0.5.

Preferably, the mass ratio of chlorogenic acid to coumaroylquinic acid is 100:0.01-0.1.

More preferably, the mass ratio of chlorogenic acid to coumaroylquinic acid is 100:0.05.

The present invention provides a method for preparation of the pharmaceutical composition mentioned above, and it is a commonly used pharmaceutical preparation obtained by using chlorogenic acid and coumaroylquinic acid as the active ingredients, with the addition of pharmaceutically acceptable excipients.

Preferably, said preparation is an oral or injectable preparation.

The present invention provides the use of the pharmaceutical composition mentioned above in the preparation of drugs for treatment of sarcoma.

Where, said sarcoma includes osteosarcoma, fibrosarcoma, liposarcoma, and rhabdomyosarcoma. Chlorogenic acid according to the present invention can effectively treat sarcoma, and by systemic+local administration ways, the therapeutic effect is better than that of the chemotherapeutic drug adriamycin. Moreover, chlorogenic acid has been proven to be a safe drug with very little side effects, and it can replace traditional chemotherapeutics and be used for the treatment of sarcomas. Chlorogenic acid can effectively solve the problem of high side effects of traditional chemotherapeutics in the treatment of sarcomas, and has a good clinical application prospect.

Chlorogenic acid composition of the present invention, containing chlorogenic acid and coumaroylquinic acid, can effectively treat sarcoma and has a better therapeutic effect than the chemotherapeutic drug adriamycin. The experimental results of the present invention show that the combined use of chlorogenic acid and coumaroylquinic acid can exert a synergistic effect. Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

Figure 1:
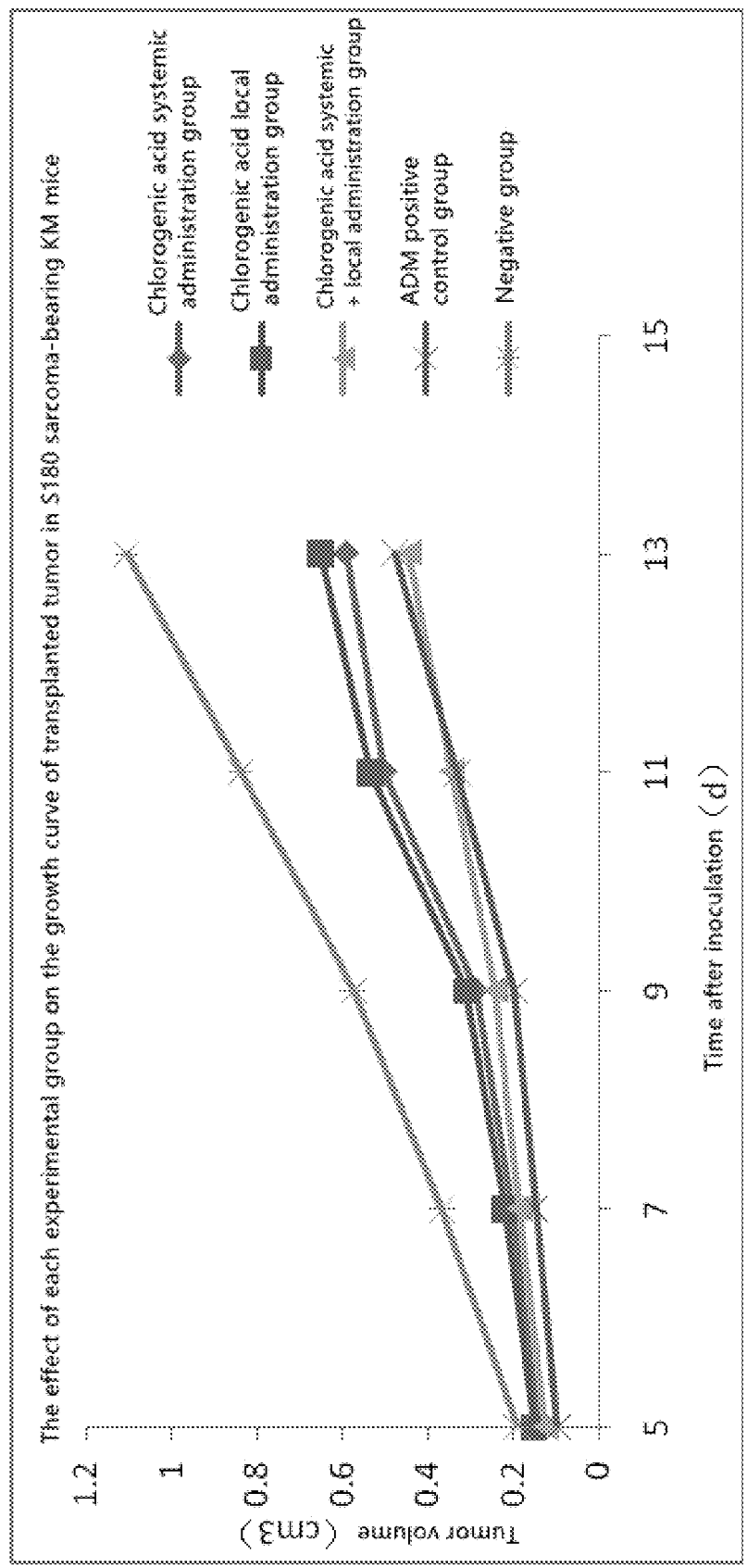
FIG. 1. The effect of each experimental group in experimental example 1 on the growth curve of transplanted tumor in S180 sarcoma-bearing KM mice.

The starting materials and equipment used in the specific examples of the present invention are all known products and can be obtained by purchasing commercially available products.

Example 1 The formula for oral preparation of the pharmaceutical composition according to the present invention 1. Formula 1

Chlorogenic acid 1000 g, coumaroylquinic acid 1 g.

Preparative method: chlorogenic acid and coumaroylquinic acid were aseptically weighed according to the formula, mixed thoroughly, and aseptically subpacked as powders.

2. Formula 2

Chlorogenic acid 1000 g, coumaroylquinic acid 5 g, bulking agent 500 g, binding agent 5 g.

Preparative method: chlorogenic acid, coumaroylquinic acid, bulking agent, and binding agent were weighed according to the formula, granulated, sieved, and subpacked as granules.

3. Formula 3

Chlorogenic acid 1000 g, coumaroylquinic acid 1 g, bulking agent 500 g, binding agent 5 g, and lubricant 3 g.

Preparative method: chlorogenic acid, coumaroylquinic acid, bulking agent, and binding agent were weighed according to the formula, granulated, sieved, and then lubricant was added, followed by pressing, to obtain tablets.

Above bulking agents were one or more of mannitol, lactose, starch, microcrystalline cellulose, and dextrin; the binding agents were sodium carboxymethylcellulose and PVP; the lubricants were magnesium stearate, talcum powder, and micro silica gel.

Example 2 The formula for injection of the pharmaceutical composition according to the present invention 1. Formula 1

Chlorogenic acid 1000 g, coumaroylquinic acid 1 g.

Preparative method (1): chlorogenic acid and coumaroylquinic acid were aseptically weighed according to the formula, mixed thoroughly, and aseptically subpacked as powder injection.

Preparative method (2): chlorogenic acid and coumaroylquinic acid were weighed according to the formula, dissolved in water for injection, filtered, sterilized, and freeze-dried to obtain freeze-dried powder injection.

2. Formula 2

Chlorogenic acid 1000 g, coumaroylquinic acid 1 g, support agent 2667 g, and antioxidant 67 g.

Preparative method: chlorogenic acid, coumaroylquinic acid, support agent, and antioxidant were weighed according to the formula, dissolved in water for injection, filtered, sterilized, and freeze-dried to obtain freeze-dried powder injection.

Said support agents were mannitol, lactose and glucose; the antioxidants were sodium bisulfite, vitamin, glutathione, and folic acid.

In the following, the beneficial effect of the present invention was proved by experimental examples: Experimental example 1 In vivo study on the inhibitory effect of chlorogenic acid on S180 sarcoma transplantation in KM mice 1. Experimental Materials 1) Animals KM mice, half male and half female, weighing 17-24 g.

2) Cell Lines

S180 cell lines were mouse sarcoma cells, and suspendedly grew in DH medium, containing 20% calf serum, 1 mmol/L glutamine, 100 U·ml$^{-1}$ penicillin, and 100 μg·ml$^{-1}$ streptomycin, then cultured in 37° C. 5% $CO_2$, saturated humidity incubator. The medium was changed every 2-3 days for passage.

3) Drugs

Chlorogenic acid, adriamycin (ADM), physiological saline.

2. Experimental Method

1) Cell Culture

S180 cells in the logarithmic growth phase were harvested, centrifuged at 1000 rpm for 5 min, washed twice, and the number of viable cells was counted by trypan blue staining. The cells were inoculated into the abdominal cavity of KM mice as soon as possible, and these mice were used as breeding mice. 2) In vivo experiment The ascites was extracted from 7 to 10 days, and the number of cells was adjusted to (about $1 \times 10^6$ cells) after dilution. The cell suspension in ascites was inoculated subcutaneously in the axillary of the left forelimb of the mice at 0.2 ml/animal. The animals were randomly grouped according to their body weight, 10 mice for each group, namely the chlorogenic acid group, the ADM group (2 mg·kg$^{-1}$), and the negative group (N.S), and the mice were administrated on the second day after inoculation. Chlorogenic acid systemic administration group: intravenously injected, once a day, at a dose of 30 mg·kg$^{-1}$.

Chlorogenic acid local administration group: subcutaneously injected into the periphery of the in situ lesion, once a day, at a dose of 30 mg·kg$^{-1}$.

Chlorogenic acid systemic+local administration group: intravenously injected, once a day, at a dose of 30 mg·kg$^{-1}$; subcutaneously injected into the periphery of the in situ lesion, once every 5 days, at a dose of 30 mg·kg$^{-1}$.

ADM group: intraperitoneally injected, once a day, at a dose of 2 mg·kg$^{-1}$.

Negative group: intraperitoneally injected, once a day, receiving an equal volume of normal saline. On the 5th day after inoculation, the tumor volume was measured ($V=0.52 \times L$ (the long diameter of the transplanted tumor)$\times W^2$ (the shortest diameter of the transplanted tumor)), and the mice were weighed every three days. The experiment was terminated when the average tumor size in the negative group was more than 1 g (the tumor volume was about 0.5 cm$^3$). The mice were sacrificed by cervical vertebra luxation and weighed, the tumor was removed, and the tumor inhibitory rate was calculated. Tumor inhibitory rate %=[1−(average tumor weight in drug group/average tumor weight in negative group)]×100%.

3. Experimental Results

1) Effect of each experimental group on the growth volume of transplanted tumor in S180 sarcoma-bearing KM mice See Table 1 and FIG. 1.

TABLE 1

Effect of each experimental group on the growth volume of transplanted tumor in S180 sarcoma-bearing KM mice ($\bar{x} \pm s$, n = 10).

| Time after inoculation | Chlorogenic acid systemic administration group | Chlorogenic acid local administration group | Chlorogenic acid systemic + local administration group | ADM 2 mg·kg$^{-1}$ | Negative group |
|---|---|---|---|---|---|
| 5 d | 0.141 ± 0.032 | 0.152 ± 0.028 | 0.125 ± 0.038 | 0.096 ± 0.041** | 0.191 ± 0.071 |
| 7 d | 0.205 ± 0.061* | 0.221 ± 0.047* | 0.186 ± 0.065* | 0.148 ± 0.066** | 0.367 ± 0.151 |
| 9 d | 0.289 ± 0.082* | 0.311 ± 0.064* | 0.243 ± 0.066** | 0.199 ± 0.080** | 0.574 ± 0.293 |
| 11 d | 0.504 ± 0.158** | 0.535 ± 0.078** | 0.344 ± 0.127** | 0.333 ± 0.159** | 0.839 ± 0.202 |
| 13 d | 0.593 ± 0.213** | 0.651 ± 0.154** | 0.446 ± 0.157** | 0.478 ± 0.241** | 1.106 ± 0.195 |

Each drug group was compared with the negative group,
*p < 0.05,
**p < 0.001

As shown in Table 1 and FIG. 1:
(1) Chlorogenic acid systemic administration group, local administration group, systemic+local administration group, and ADM positive control group had significant inhibitory effect on the growth volume of transplanted tumors in S180 sarcoma-bearing KM mice at different time points in the experimental process, and compared with negative control group, had statistical difference;
(2) Chlorogenic acid systemic+local administration group had better inhibitory effect on the growth volume of transplanted tumors in S180 sarcoma-bearing KM mice than the systemic administration group and the local administration group;
(3) Chlorogenic acid systemic+local administration group had similar inhibitory effect on the growth volume of transplanted tumors in S180 sarcoma-bearing KM mice to that of ADM positive control group.

Figure 2:
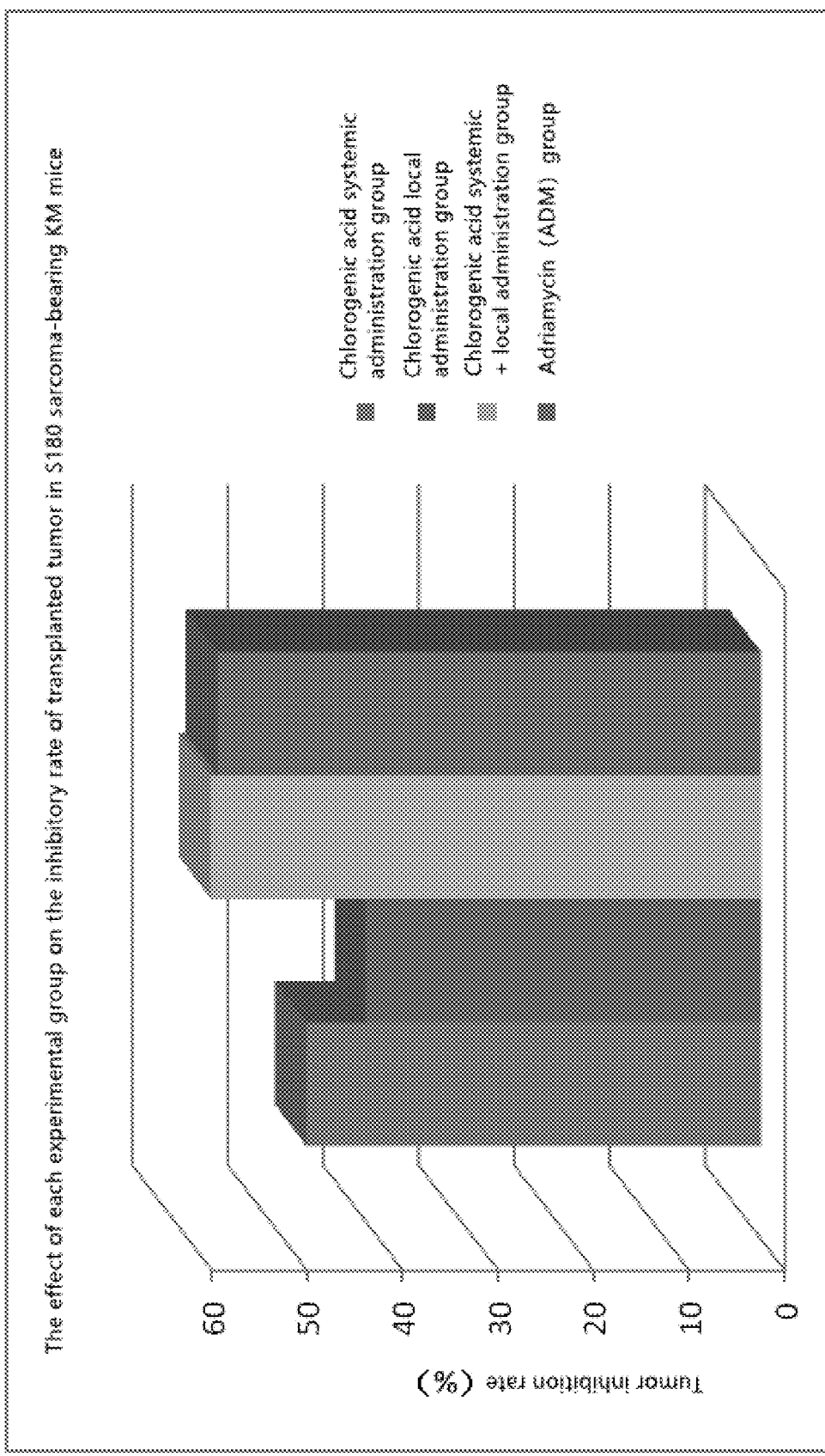
FIG. 2. The effect of each experimental group in experimental example 1 on the inhibitory rate of transplanted tumor in S180 sarcoma-bearing KM mice.

2) Effect of each experimental group on the weight and inhibitory rate of transplanted tumor in S180 sarcoma-bearing KM mice See Table 2 and FIG. 2.

TABLE 2

Effect of each experimental group on the weight and inhibitory rate of transplanted tumor in S180 sarcoma-bearing KM mice

| Groups | Dose (mg·kg$^{-1}$) | Tumor weight (g) | Tumor inhibiton rate(%) |
|---|---|---|---|
| Chlorogenic acid systemic administration group | 30 | 1.183 ± 0.215*** | 47.61 |
| Chlorogenic acid local administration group | 30 | 1.324 ± 0.239*** | 41.36 |
| Chlorogenic acid systemic + local administration group | 30 | 0.957 ± 0.308*** | 57.62 |
| Adriamycin (ADM) group | 2 | 0.972 ± 0.362*** | 56.95 |
| Negative group | N.S | 2.258 ± 0.547 | — |

Compared with negative group,
***p < 0.001

As shown in Table 2 and FIG. 2, the tumor inhibitory rates of chlorogenic acid systemic administration group, local administration group, systemic+local administration group, and ADM positive control group on transplanted tumors in S180 sarcoma-bearing KM mice were all higher than 40%; and the tumor inhibitory rate of chlorogenic acid systemic+ local administration group was highest, and reached 57%.

Above experiments indicated that chlorogenic acid had obvious inhibitory effect on sarcoma in mice, and when the administration mode is systemic+local administration, the inhibition effect was the best. Thus, chlorogenic acid can be used in the treatment of sarcoma.

Experimental example 2 In vivo study on the inhibitory effect of chlorogenic acid composition on
S180 sarcoma transplantation in KM mice
1 Experimental Materials
1) Animals
KM mice, half male and half female, weighing 17-24 g.
2) Cell lines
S180 cell lines were mouse sarcoma cells, and suspendedly grew in DH medium, containing 20% calf serum, 1 mmol/L glutamine, 100 U·ml$^{-1}$ penicillin, and 100 μg·ml$^{-1}$ streptomycin, then cultured in 37° C., 5% $CO_2$, saturated humidity incubator. The medium was changed every 2-3 days for passage.
3) Drugs
Chlorogenic acid, coumaroylquinic acid, chlorogenic acid: coumaroylquinic acid (weight ratio 100:0.5), chlorogenic acid: coumaroylquinic acid (weight ratio 100:0.1), chlorogenic acid: coumaroylquinic acid (weight ratio 100: 0.05), chlorogenic acid: coumaroylquinic acid (weight ratio 100:0.01), adriamycin (ADM), physiological saline.
2. Experimental Method
1) Cell culture
S180 cells in the logarithmic growth phase were harvested, centrifuged at 1000 rpm for 5 min, washed twice, and the number of viable cells was counted by trypan blue staining. The cells were inoculated into the abdominal cavity of KM mice as soon as possible, and these mice were used as breeding mice.
2) In Vivo Experiment
The ascites was extracted from 7 to 10 days, and the number of cells was adjusted to (about $1 \times 10^6$ cells) after dilution. The cell suspension in ascites was inoculated subcutaneously in the axillary of the left forelimb of the mice at 0.2 ml/animal. The animals were randomly grouped according to their body weight, 10 mice for each group, namely the chlorogenic acid group, coumaroylquinic acid group, chlorogenic acid+coumaroylquinic acid combination group, ADM group (2 mg·kg$^{-1}$), and the negative group (N.S), and the mice were administrated on the second day after inoculation. Chlorogenic acid group: intraperitoneally injected, once a day, at a dose of 30 mg·kg$^{-1}$. Coumaroylquinic acid group: intraperitoneally injected, once a day, at a dose of 30 mg·kg$^{-1}$.
Chlorogenic acid+coumaroylquinic acid combination group: intraperitoneally injected, once a day, at a dose of 30 mg·kg$^{-1}$.

ADM group: intraperitoneally injected, once a day, at a dose of 2 mg·kg$^{-1}$.

Negative group: intraperitoneally injected, once a day, receiving an equal volume of normal saline.

On the 5th day after inoculation, the tumor volume was measured (V=0.52×L (the long diameter of the transplanted tumor)×W$^2$ (the shortest diameter of the transplanted tumor)), and the mice were weighed every three days. The experiment was terminated when the average tumor size in the negative group was more than 1 g (the tumor volume was about 0.5 cm$^3$). The mice were sacrificed by cervical vertebra luxation and weighed, the tumor was removed, and the tumor inhibitory rate was calculated. Tumor inhibitory rate %=[1−(average tumor weight in drug group/average tumor weight in negative group)]×100%.

3. Experimental Results

Figure 3:
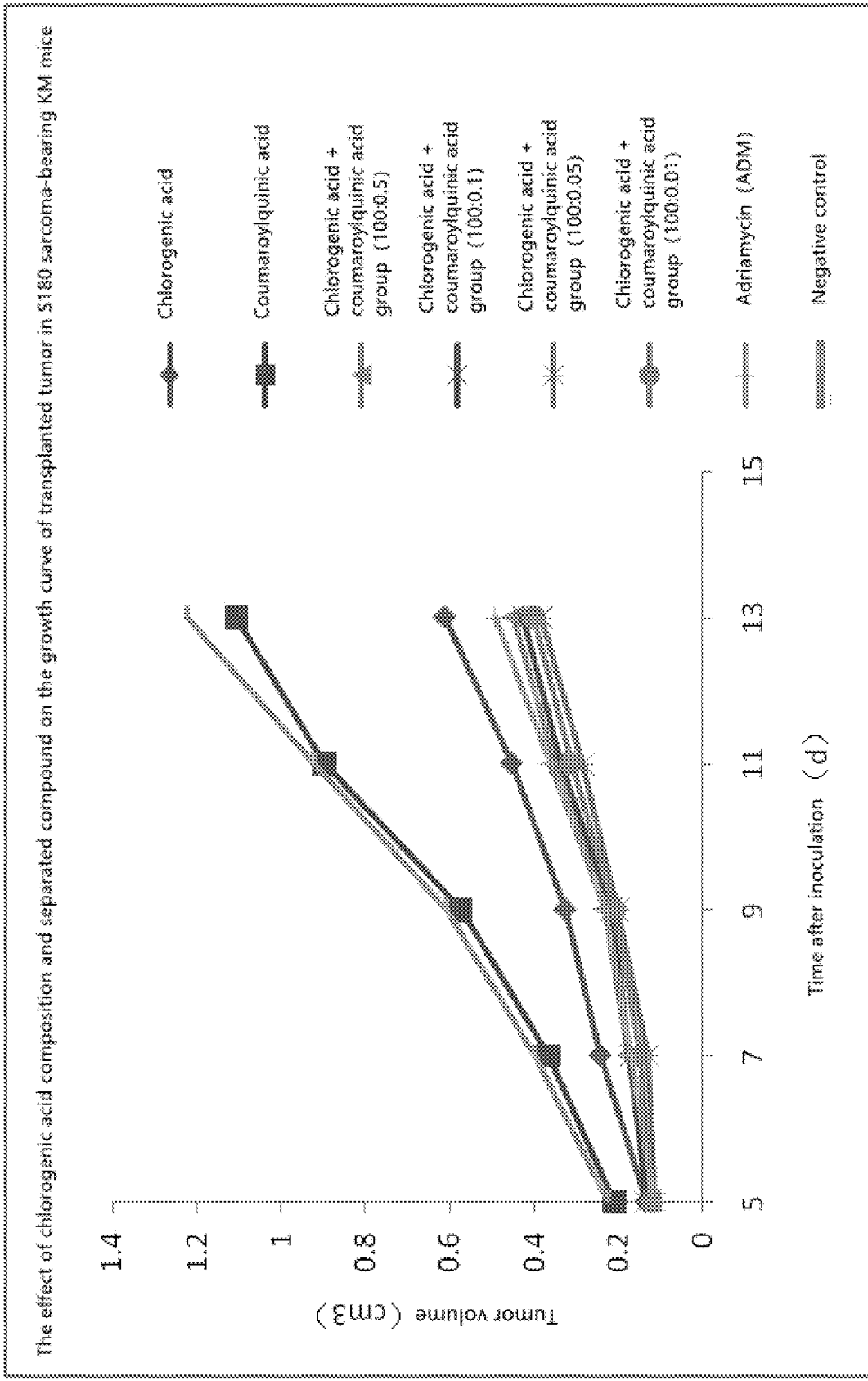
FIG. 3. The effect of each experimental group in experimental example 2 on the growth curve of transplanted tumor in S180 sarcoma-bearing KM mice.

1) Effect of Each Experimental Group on the Growth Volume of Transplanted Tumor in S180 Sarcoma-Bearing KM Mice See Table 3 and FIG. 3.

TABLE 3

Effect of each experimental group on the growth volume of transplanted tumor in S180 sarcoma-bearing KM mice (x ± s, n = 10).

| Time after inocu-lation | Chlorogenic acid | Coumaroylquinic acid | Chlorogenic acid * Coumaroylquinic acid group (100:0.5) | Chlorogenic acid * Coumaroylquinic acid group (100:0.1) | Chlorogenic acid * Coumaroylquinic acid group (100:0.05) | Chlorogenic acid * Coumaroylquinic acid group (100:0.01) | ADM 2 mg · kg$^{-1}$ | Negative control |
|---|---|---|---|---|---|---|---|---|
| 54 | 0.135 ± 0.078 | 0.209 ± 0.058 | 0.124 ± 0.062 | 0.133 ± 0.032 | 0.114 ± 0.052* | 0.121 ± 0.041 | 0.116 ± 0.073** | 0.224 ± 0.052 |
| 74 | 0.242 ± 0.053* | 0.364 ± 0.074 | 0.175 ± 0.0751* | 0.172 ± 0.028** | 0.131 ± 0.038* | 0.148 ± 0.052* | 0.171 ± 0.082** | 0.397 ± 0.083 |
| 94 | 0.326 ± 0.071* | 0.573 ± 0.093 | 0.232 ± 0.091* | 0.218 ± 0.071* | 0.202 ± 0.068* | 0.209 ± 0.046* | 0.231 ± 0.053** | 0.688 ± 0.225 |
| 114 | 0.453 ± 0.093** | 0.898 ± 0.075 | 0.351 ± 0.115** | 0.337 ± 0.064** | 0.296 ± 0.077** | 0.312 ± 0.092** | 0.363 ± 0.128** | 0.924 ± 0.162 |
| 134 | 0.811 ± 0.142** | 1.106 ± 0.137 | 0.448 ± 0.126** | 0.426 ± 0.089** | 0.382 ± 0.083** | 0.401 ± 0.103** | 0.492 ± 0.204** | 1.223 ± 0.156 |

Each drug group was compared with the negative group, *p<0.05, ** p<0.001

As shown in Table 3 and FIG. 3:

(1) Chlorogenic acid group, group, chlorogenic acid+coumaroylquinic acid group, and ADM positive control group had significant inhibitory effect on the growth volume of transplanted tumors in S180 sarcoma-bearing KM mice at different time points in the experimental process, and compared with negative control group, had statistical difference;

(2) Coumaroylquinic acid group didn't show inhibitory effect on the growth volume of transplanted tumor in S180 sarcoma-bearing KM;

(3) Chlorogenic acid+coumaroylquinic acid group had better inhibitory effect on the growth volume of transplanted tumors in S180 sarcoma-bearing KM mice than chlorogenic acid group and ADM positive control group.

Figure 4:
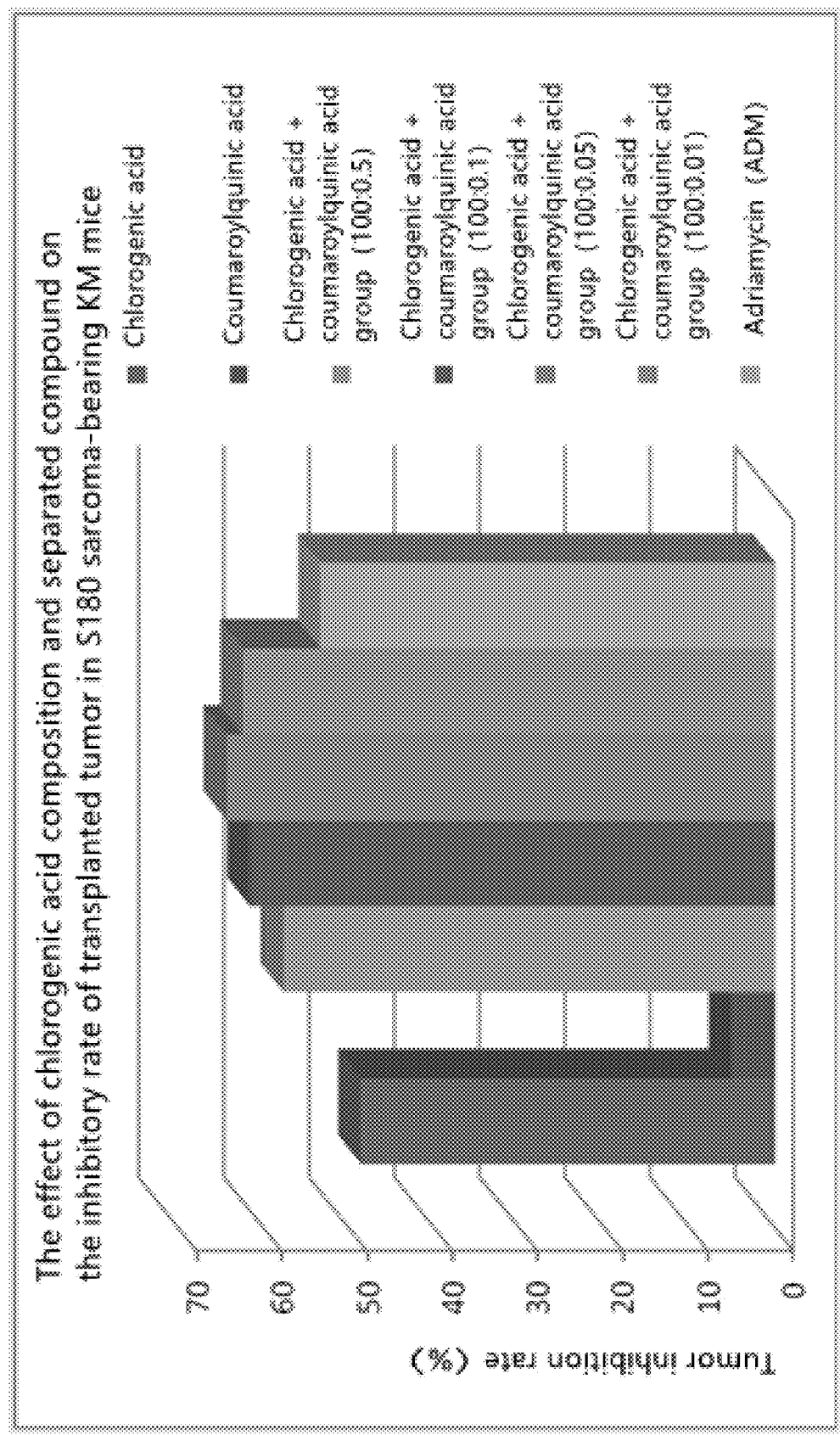
FIG. 4. The effect of each experimental group in experimental example 2 on the inhibitory rate of transplanted tumor in S180 sarcoma-bearing KM mice.

2) Effect of each experimental group on the weight and inhibitory rate of transplanted tumor in S180 sarcoma-bearing KM mice See Table 4 and FIG. 4.

TABLE 4

Effect of each experimental group on the weight and inhibitory rate of transplanted tumor in S180 sarcoma-bearing KM mice

| Groups | Dose (mg · kg$^{-1}$) | Tumor weight (g) | Tumor inhibition rate (%) |
|---|---|---|---|
| Chlorogenic acid group | 30 | 1.247 ± 0.583*** | 48.64 |
| Coumaroylquinic acid group | 30 | 2.303 ± 0.475*** | 5.15 |
| Chlorogenic acid + coumaroylquinic acid (100:0.5) group | 30 | 1.026 ± 0.621*** | 57.74 |
| Chlorogenic acid + coumaroylquinic acid (100:0.1) group | 30 | 0.931 ± 0.436*** | 61.66 |
| Chlorogenic acid + coumaroylquinic acid (100:0.05) group | 30 | 0.864 ± 0.774*** | 64.42 |
| Chlorogenic acid + coumaroylquinic acid (100:0.01) group | 30 | 0.991 ± 0.529*** | 62.48 |
| Adriamycin (ADM) group | 2 | 1.132 ± 0.552*** | 53.38 |
| Negative group | N.S | 2.428 ± 0.818 | — |

Compared with negative group,
***p < 0.001

As shown in Table 4 and FIG. 4, the tumor inhibitory rates of chlorogenic acid group, chlorogenic acid+coumaroylquinic acid group, and ADM positive control group on transplanted tumors in S180 sarcoma-bearing KM mice were all higher than 45%; the inhibitory rate of coumaroylquinic acid group was lowest, and only 5%; the inhibitory rate of chlorogenic acid+coumaroylquinic acid group was highest, indicating the best inhibitory effect, and reached 64%.

At the same dosage, chlorogenic acid+coumaroylquinic acid group was superior to chlorogenic acid group and coumaroylquinic acid group, indicating that the combination of chlorogenic acid+coumaroylquinic acid has a synergistic effect. Among them, the weight ratio of chlorogenic acid and coumaroylquinic acid is preferably 100: (0.01-0.1), and more preferably 100:0.05. Above experiment showed that chlorogenic acid composition of the present invention had a significant inhibitory effect on mouse sarcoma, and the inhibitory effect was better than that of adriamycin (ADM). Thus, chlorogenic acid composition of the present invention can be used to treat sarcoma, and the therapeutic effect was excellent.

In summary, chlorogenic acid according to the present invention can effectively treat sarcoma, and by systemic+ local administration mode, the therapeutic effect was better than that of the chemotherapeutic drug adriamycin. Moreover, chlorogenic acid has been proven to be a safe drug with very little side effects, and it can replace traditional chemotherapeutics and be used for the treatment of sarcomas. Chlorogenic acid can effectively solve the problem of high side effects of traditional chemotherapeutics in the treatment of sarcomas, and has a good clinical application prospect.

Chlorogenic acid composition of the present invention, containing chlorogenic acid and coumaroylquinic acid, can effectively treat sarcoma and has a better therapeutic effect than the chemotherapeutic drug adriamycin. The experimental results of the present invention show that the combined use of chlorogenic acid and coumaroylquinic acid can exert a synergistic effect.

The invention claimed is:

1. A method for treating sarcoma, comprising administering a pharmaceutical composition to a subject in need thereof, wherein the pharmaceutical composition comprises a sole active ingredient and one or more pharmaceutically acceptable excipient or auxiliary, wherein the sole active ingredient consists of chlorogenic acid and coumaroylquinic acid at a mass ratio of chlorogenic acid to coumaroylquinic acid of 100:0.01-0.5.

2. The method according to claim 1, wherein the sarcoma is osteosarcoma, fibrosarcoma, liposarcoma, or rhabdomyosarcoma.

3. The method according to claim 2, wherein the sarcoma is osteosarcoma, fibrosarcoma, or liposarcoma.

4. The method according to claim 1, wherein the pharmaceutical composition consists of the sole active ingredient and the one or more pharmaceutically acceptable excipient or auxiliary.

5. The method according to claim 1, where the mass ratio of chlorogenic acid to coumaroylquinic acid is 100:0.01-0.1.

6. The method according to claim 5, wherein the mass ratio of chlorogenic acid to coumaroylquinic acid is 100:0.01.

7. The method according to claim 5, wherein the mass ratio of chlorogenic acid to coumaroylquinic acid is 100:0.05.

8. The method according to claim 1, wherein the sarcoma is osteosarcoma, fibrosarcoma, or liposarcoma.

* * * * *